(12) United States Patent
Reichert et al.

(10) Patent No.: US 7,736,866 B2
(45) Date of Patent: Jun. 15, 2010

(54) ENZYME-BASED TIME TEMPERATURE INDICATOR

(75) Inventors: Hans Reichert, Rheinfelden (DE); Peter Simmendinger, Basel (CH); Thomas Bolle, Efringen-Kirchen (DE)

(73) Assignee: Ciba Corporation, Tarrytown, NY (US)

( * ) Notice: Subject to any disclaimer, the term of this patent is extended or adjusted under 35 U.S.C. 154(b) by 605 days.

(21) Appl. No.: 11/659,645

(22) PCT Filed: Aug. 3, 2005

(86) PCT No.: PCT/EP2005/053784

§ 371 (c)(1),
(2), (4) Date: Feb. 7, 2007

(87) PCT Pub. No.: WO2006/015961

PCT Pub. Date: Feb. 16, 2006

(65) Prior Publication Data

US 2009/0226948 A1    Sep. 10, 2009

(30) Foreign Application Priority Data

Aug. 11, 2004  (EP) .................................. 04103870

(51) Int. Cl.
*C12Q 1/34* (2006.01)
(52) U.S. Cl. ....................................................... 435/18
(58) Field of Classification Search .................. None
See application file for complete search history.

(56) References Cited

U.S. PATENT DOCUMENTS

| | | | |
|---|---|---|---|
| 2,671,028 A | 3/1954 | Clark | 99/192 |
| 3,977,945 A | 8/1976 | Törnmarck | 195/127 |
| 4,184,920 A | 1/1980 | Blixt et al. | 435/19 |
| 4,826,762 A | 5/1989 | Klibanov et al. | 435/28 |
| 5,739,004 A | 4/1998 | Woodson | 435/31 |
| 2002/0123005 A1 | 9/2002 | Ichimura et al. | 430/281.1 |

FOREIGN PATENT DOCUMENTS

| | | |
|---|---|---|
| EP | 0 892 018 | 1/1999 |
| EP | 1 281 731 | 2/2003 |
| WO | 92/05415 | 4/1992 |
| WO | 02/056923 | 7/2002 |

OTHER PUBLICATIONS

Litman et al."An internally referenced test strip immunoassay for morphine", Clin. Chem. 1983, 29(9):1598-1603.*
Bais et al. "Urinary glycolate measured by use of (S)-2-hydroxy-acid oxidase", Clin. Chem. 1985, 31/5:710-713.*
V. Hall-Goulle et al., "Latent pigments and their applications", Research Disclosure, vol. 428, No. 92, (Dec. 1999).
M. Hendrickx et al., International Journal of Food Science and Technology, vol. 27, No. 1, pp. 21-31, (1992).
S. F. De Cordt et al., Journal of Chemical Technology and Biotechnology, vol. 59, No. 2, pp. 193-199, (Feb. 1994).
S. De Cordt et al., Biotechnology and Bioengineering, vol. 40, No. 3, pp. 396-402, (Jul. 1992).

* cited by examiner

*Primary Examiner*—Karen Cochrane Carlson
*Assistant Examiner*—Bin Shen
(74) *Attorney, Agent, or Firm*—Joseph C. Suhadolnik

(57) ABSTRACT

A time temperature indicator for indicating temperature change over time is provided, comprising an immobilized enzyme and a substrate of the enzyme, wherein the reaction of the substrate catalyzed by the enzyme produces a reaction product in a time and temperature dependent manner and wherein the formation of the reaction product can be detected by monitoring a physical characteristic of the substrate and/or the product which is linked to its concentration. Also provided is a method of time temperature indication comprising the step of an enzyme-catalyzed reaction, a method of printing the enzyme-based time temperature indicator on a packaging material or a label, a printing ink or printing ink concentrate comprising components of the enzyme-based time temperature indicator and a packaging material or a label comprising the enzyme-based time temperature indicator.

5 Claims, No Drawings

ENZYME-BASED TIME TEMPERATURE INDICATOR

The present invention relates to an enzyme-based time temperature indicator, a method of time temperature indication comprising the step of an enzyme-catalyzed reaction and a method of printing the enzyme-based time temperature indicator on a packaging material or a label. The present invention further relates to printing inks or printing ink concentrates comprising components of the enzyme-based time temperature indicator and a packaging material or a label comprising at least one component of the enzyme-based time temperature indicator.

When perishable materials are used it is often desirable to ascertain the age and the current usable condition of the materials. While the application of an expiry date to the packaging was formerly considered sufficient, for a large number of products such a procedure is nowadays too inaccurate and insufficiently tamper-proof. In particular, the condition of perishable products is generally a function not only of time but also of other variables, such as, especially, temperature.

U.S. Pat. No. 3,999,946 addresses this problem and proposes providing the perishable products with an indicator giving the time/temperature history. According to the length of storage and the storage temperature of the product, the originally colourless acetylene-based indicator exhibits a characteristic, irreversible colour change from which the quality of the stored perishable product can be inferred.

U.S. Pat. No. 5,053,339 (WO 92/09870) describes a time-temperature indicator (TTI) which consists of a layer comprising the indicator, a barrier layer that is impermeable to the indicator and permeable to the activator, and a layer comprising the activator. In dependence upon the temperature, the activator diffuses through the barrier layer into the indicator layer, where it provides a change in colour.

WO 99/39197 relates to a substrate for the packaging of, or for application to, ageing- and temperature-sensitive products, the substrate having, arranged in the region of the substrate, a planar time-temperature indicator comprising a matrix and at least one reversible indicator embedded therein, the indicator having photochromic properties based on transfer reactions. The nature and the amount of the TTI used for printing can be matched to the perishable products. Furthermore, the TTI can be used in the form of a solution and/or in the form of an aqueous dispersion.

There are also approaches known in the prior art that use the action of an enzyme on a substrate to produce a color change as the temperature increases. Hoffman, U.S. Pat. No. 2,553,369 teaches the use of a starch digesting enzyme to hydrolyze a starch-indole complex so that its characteristic color disappears. These components are dissolved in a water solution. In the device of Clark, U.S. Pat. No. 2,671,028, the action of the enzyme on the substrate with increasing temperature causes a change in pH, thereby triggering a color change in an indicator. These components are again in a water solution. In GB Pat. No. 1,366,797 the device which is activated upon freezing contains, in a water solution, appropriate enzyme and substrate to produce ammonia gas which diffuses through a semipermeable diaphragm whose permeability increases with an increase in temperature. The ammonia reacts with a pH indicator on the other side of the diaphragm.

Further, in U.S. Pat. No. 4,826,762 Klibanov et al. teach indicators of temperature change over time which are used to monitor the shipping and handling conditions of perishable items. More specifically, the disclosure in U.S. Pat. No. 4,826,762 relates to a temperature change indicator composed of an enzyme and a substrate for that enzyme suspended in a solid organic solvent or mixture of solvents as a support medium. The organic solvent or solvents are chosen so as to melt at a specific temperature or in a specific temperature range. When the temperature of the indicator is elevated above the chosen, or critical temperature, the solid organic solvent support will melt, and the enzymatic reaction will occur, producing a visually detectable product which is stable to further temperature variation.

Livesley in WO 92/05415 also describes time temperature indicators, for example for indicating product life, in which a label, embodied directly in or applied to a package, carries a substrate which is catalysed by an enzyme laid down in a progressive concentration to produce directly a differently coloured reaction product, the development of which progresses along or around the label in accordance with time and temperature conditions. The label may have the following physical formats: (1) a self adhesive paper label, where the paper is impregnated with the enzyme substrate, and then the enzyme solution is applied to the label using one of a variety of printing techniques to give a single layer label with the required graphics. The finished labels may then be stored frozen until applied to a food package; (2) a self adhesive label impregnated with the enzyme substrate, and a clear self adhesive laminate label printed with the required enzyme pattern, wherein lamination of the two label layers activates the enzyme reaction; (3) a paper label containing the enzyme substrate may be laminated on to the product package, during the production process, and then overprinted with the enzyme solution; and (4) the enzyme substrate may be directly incorporated into an ink formulation, such that it constitutes a label directly printed onto the packaging material and the enzyme solution may then be overprinted on to the substrate patch at a convenient later time, using a second ink formulation.

However a major disadvantage of using enzymes results from the fact that they are expensive and relatively unstable compared to most chemical compounds, even when they are used in aqueous media where enzymes normally function. In addition, enzymes are difficult to store in a manner that retains their activity and functional integrity, for commercially reasonable periods of time (months to years) without having to resort to refrigeration (−80° C. to liquid N2 temperatures), or to maintenance in aqueous solvents of suitable ionic strength, pH, etc. The enzyme-based time temperature indicators in the prior art carry out the enzymatic reaction in the homogeneous format of a liquid solution wherein the conditions like ionic strength, buffer, concentration of metal ions are dictated by the requirements of the reaction. The presence of stabilizing agents like glycerol, chelate-forming reagents etc. necessary to keep the enzyme in solution stable for days or weeks generally impede or at least retard the enzymatic reactivity.

Thus, there is a need for an enzyme-based time temperature indicator (TTI) wherein the amount of enzyme necessary for the enzymatic reaction can be kept as low as possible and wherein the enzyme can be stored and handled before and after the TTI is activated in a manner which avoids inactivation and/or proteolytic degradation. Starting from that prior art, the problem underlying the invention is therefore to provide an enzyme-based time temperature indicator which is relatively inexpensive and simply to handle and which enables the quality of the labeled products to be accurately determined.

The problem according to the invention is solved by a time temperature indicator for indicating temperature change over time that comprises an immobilized enzyme and a substrate of the enzyme, wherein the reaction of the substrate catalyzed by the enzyme produces a reaction product in a time and temperature dependent manner and wherein the formation of the reaction product can be detected by monitoring a physical characteristic of the substrate and/or the product which is linked to its concentration. The physical characteristic can be any inherent property of the substrate and/or the reaction product provided it produces a detectable signal, allows to distinguish substrate and reaction product and corresponds to the concentration of at least one of them such that the detectable signal shed light on the reaction progress.

In a preferred embodiment, the time temperature indicator according to the invention is based on an enzyme-catalyzed reaction that produces a reaction product at different color to the substrate. For example, the substrate is pale or colorless and the reaction product is colored. Alternatively, the substrate is colored and the reaction product is pale or colorless. However, the physical characteristic of the substrate and/or the product which is linked to its concentration is not limited to a color of the visible spectrum but also includes absorption and/or emission at a wavelength within the IR or UV range.

Preferably, the time temperature indicator according to the invention further comprises a buffer system and/or enzyme-specific cofactors. Once the TTI is assembled, the enzymatic reaction is preferably buffered at a pH from about 6.5 to about 9.5. Since the total process of time temperature indication occurs in either base or acid buffered systems, suitable buffers include phosphate, N-2-hydroxyethylpiperazine-N'-2-ethanesulfonic acid (HEPES), 3-(N-morpholino)propanesulfonic acid (MOPS), tris(hydroxymethyl)-aminomethane (TRIS), N-tris(hydroxymethyl)-methyl-2-aminoethanesulfonic acid (TES), N-2-hydroxyethylpiperazinepropanesulfonic acid (EPPS), diethanolamine and dimethyl glutarate. Additional materials such as stabilizing agents and other conventional additives, can be employed if desired.

The time temperature indicator according to the invention preferably comprises an enzyme that catalyzes the conversion of a substrat to produce directly a differently colored reaction product. The enzyme can be an oxidoreductase, a transferase, a hydrolase, a lyase, an isomerases or a ligase.

Oxidoreductases catalyse oxido-reductions. The substrate oxidised is regarded as an hydrogen or electron donor. Generally, these enzymes are classified by the donor group that undergoes oxidation or by the acceptor. Dehydrogenase is another name often used for these enzymes. The name oxidase is only used where O(2) is the acceptor. Useful oxidoreductases of the instant invention include but are not limited to those acting on the CH—OH group of donors, acting on the aldehyde or oxo group of donors, acting on the CH—CH group of donors, acting on the CH—NH(2) group of donors, acting on the CH—NH group of donors, acting on NADH or NADPH, acting on other nitrogenous compounds as donors, acting on a sulfur group of donors, acting on diphenols and related substances as donors, acting on a peroxide as acceptor (peroxidases), acting on hydrogen as donor, acting on single donors with incorporation of molecular oxygen, acting on superoxide as acceptor, oxidizing metal ions, acting on —CH(2) groups, acting on iron-sulfur proteins as donors, acting on reduced flavodoxin as donor, acting on phosphorus in donors and acting on x-H and y-H to form an x-y bond.

Transferases are enzymes that transfer a group (e.g. a methyl or glycosyl group) from one compound (which is generally regarded as the donor) to another compound (generally regarded as the acceptor). Generally, these enzymes are classified by the donor group, or by the acceptor. Useful transferases of the instant invention include but are not limited to those transferring one-carbon groups, transferring aldehyde or ketone residues, acyltransferases, glycosyltransferases, transferring alkyl or aryl groups, other than methyl groups, transferring nitrogenous groups, transferring phosphorous-containing groups, transferring sulfur-containing groups.

Hydrolases are enzymes that catalyse the hydrolytic cleavage of C—O, C—N, C—C and some other bonds, including phosphoric anhydride bonds. Generally, these enzymes are classified by the nature of the bond hydrolysed or by the nature of the substrate. Although the systematic name always includes hydrolase, the name generally used is, in many cases, formed by the name of the substrate with the suffix -ase. It is understood that the name of the substrate with this suffix means a hydrolytic enzyme. Useful hydrolases of the instant invention include but are not limited to those acting on ester bonds, acting on glycosidic bonds, acting on ether bonds, acting on peptide bonds, acting on carbon-nitrogen bonds, other than peptide bonds, acting on acid anhydrides, acting on carbon-carbon bonds, acting on halide bonds, acting on phosphorus-nitrogen bonds, acting on sulfur-nitrogen bonds, acting on carbon-phosphorus bonds, acting on sulfur-sulfur bonds, acting on carbon-sulfur bonds.

Lyases are enzymes cleaving C—C, C—O, C—N, and other bonds by elimination, leaving double bonds or rings, or conversely adding groups to double bonds. Useful lyases of the instant invention include but are not limited to carbon-carbon lyases, carbon-oxygen lyases, carbon-nitrogen lyases, carbon-sulfur lyases, carbon-halide lyases and phosphorus-oxygen lyases.

Isomerases catalyse geometric or structural changes within one molecule. According to the type of isomerism, they are called racemases, epimerases, cis-tran-isomerases, isomerases, tautomerases, mutases or cylcoisomerases. The subclasses are generally defined according to the type of isomerism, the sub-subclasses to the type of substrates. Useful isomerases of the instant invention include but are not limited to racemases and epimerases, cis-trans-isomerases, intramolecular oxidoreductases, intramolecular transferases (so-called mutases) and intramolecular lyases.

Ligases catalyse the joining together of two molecules coupled with the hydrolysis of a pyrophosphate bond in ATP or a similar triphosphate. The bonds formed are often high-energy bonds. The subclasses are generally defined according to the type of bond formed. Useful isomerases of the instant invention include but are not limited to those forming carbon-oxygen bonds, forming carbon-sulfur bonds, forming carbon-nitrogen bonds, forming carbon-carbon bonds, forming phosphoric ester bonds, forming nitrogen-metal bonds.

Preferably, the enzyme used according to the instant invention is a hydrolase selected from the group consisting of amidases, lipases, glycosylases, carboxylic esterases and ether hydrolases.

Especially preferred are carboxylic esterase selected from the group of enzymes consisting of arylesterase, triacylglycerol lipase, lysophospholipase, acetylesterase, acetylcholinesterase, cholinesterase, L-arabinonolactonase, gluconolactonase, retinyl-palmitate esterase, acylglycerol lipase, 1,4-lactonase, galactolipase, D-arabinonolactonase, 6-phosphogluconolactonase, 4-methyloxaloacetate esterase, phorbol-diester hydrolase, methylumbelliferyl-acetate deacetylase, bis(2-ethylhexyl)phthalate esterase, L-rhamnono-1,4-lactonase and xylono-1,4-lactonase.

In a particular preferred embodiment of the instant invention is based on the enzymatic hydrolysis of lipids by the activity of a triacylglycerol lipase, preferably a pancreas triacylglycerol lipase which is followed by a color change of a pH indicator caused by a decrease of the pH value. Suitable substrates for the triacylglycerol lipase catalyzed reaction include but are not limited to glycerine tricapronate, tripelargonin, tributyrin and bis-3,5,5-trimethyl-hexyl adipate, mixed esters of polyvalent alcohols and organic and inorganic acids.

In another preferred embodiment of the instant invention use is made od amidases, preferably selected from the group consisting of arylformamidase, formyltetrahydrofolate deformylase, aryl-acylamidase, aminoacylase, 5-aminopentanamidase, hippurate hydrolase, N-methyl-2-oxoglutaramate hydrolase, alkylamidase, long-chain-fatty-acyl-glutamate deacylase, NN,N-dimethylformamidase, N-benzyloxycarbonylglycine hydrolase, urethanase, arylalkyl acylamidases which hydrolyze at least one amide bond of a pigment or dye precursor whereupon the pigment or dye is generated.

For example, the hydrolysis of the two amide bonds in Irgaphor Red 502A (see below) results in a color change from yellow of the soluble pigment precursor to orange of the pigment precipitate.

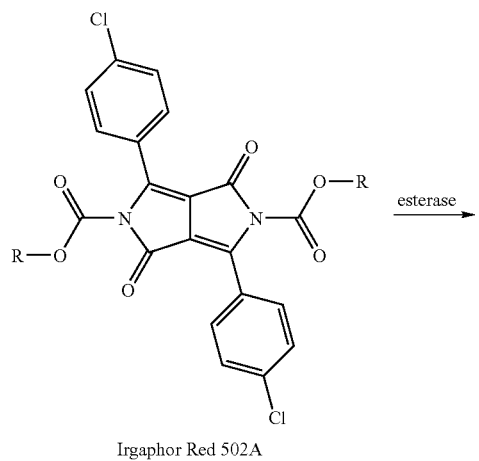

Irgaphor Red 502A

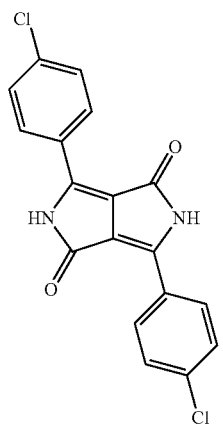

wherein R is an unsubstituted or substituted, aliphatic or aromatic residue.

Also, the Pigment Violett 37 chemistry can be used as the basis of an amidase catalyzed reaction which is accompanied with a significant color change during reaction (see below).

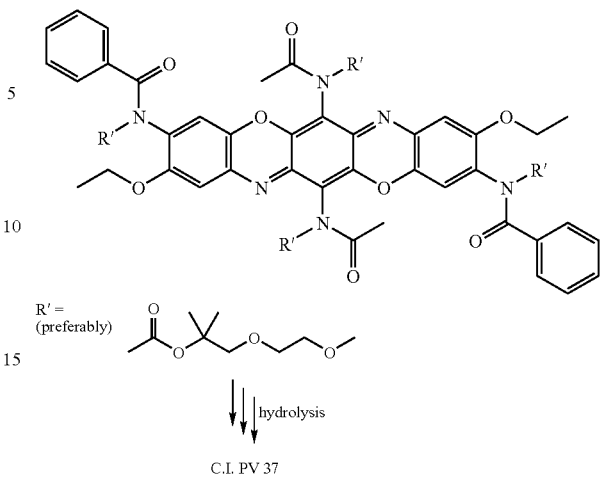

R' stands for

wherein R" is an unsubstituted or substituted, aliphatic or aromatic residue including alkoxyalkyl and alkoxyaryl.

Yet another preferred embodiment of the instant invention relates to an enzyme-based TTI wherein the substrate is selected from the group of compounds of general formula (III)

$$X\text{—}O\text{—}R''' \qquad (III)$$

wherein

X is a chromophoric group, O is oxygen and R''' stands for a sugar moiety bound to O via its glycosidic carbon atom, for an unsubstituted or substituted, aliphatic or aromatic residue, and for

wherein R" is an unsubstituted or substituted, aliphatic or aromatic residue including alkoxyalkyl and alkoxyaryl;

and wherein the enzyme is a glycosylase, an ether hydrolase or a carboxylic esterase.

The glycosylase is preferably selected from the group consisting of alpha-amylase, beta-amylase, glucan 1,4-alpha-glucosidase, endo-1,3(4-beta-glucanase, endo-1,4-beta-xylanase, dextranase, oligosaccharide alpha-1,6-glucosidase, alpha-lucosidase, beta-glucosidase, alpha-galactosidase, betagalactosidase, beta-fructofuranosidase, alpha-mannosidase, beta-mannosidase, alpha,alpha-trehalase, beta-glucuronidase, xylan endo-1,3-beta-xylosidase, amylo-alpha-1,6-glucosidase, hyaluronoglucosaminidase, hyaluronoglucuronidase, xylan 1,4-beta-xylosidase, beta-D-fucosidase, glucan endo-1,3-beta-D-glucosidase, alpha-N-acetylgalactosaminidase, alpha-N-acetylglucosaminidase, alpha-L-rhamnosidase, beta-L-rhamnosidase, glucosylceramidase, galactosylceramidase, galactosylgalactosylglucosylceramidase, sucrose alpha-glucosidase, alpha-N-arabinofuranosidase, glucan 1,3-beta-glucosidase, glucan endo-1,3- alpha-glucosidase, mannan 1,2-(1,3)-alpha-mannosidase, mannan endo-1,4-beta-mannosidase, beta-L-arabinosidase, glucan 1,3-alpha-glucosidase, 6-phospho-beta-galactosidase, 6-phospho-beta-glucosidase, maltose-6'-phosphate glucosidase, galactan 1,3-beta-galactosidase, beta-galactofuranosidase.

It is especially preferred to make use of natural occurring dye precursors to develop a dyestuff, e.g. indigo (blue color). Natural precursor of indigo is indican (from Indigofera tinctoria), a β-glucoside. β-Glucosidase, a common, commercially available enzyme easily converts the colorless precursor into the blue pigment.

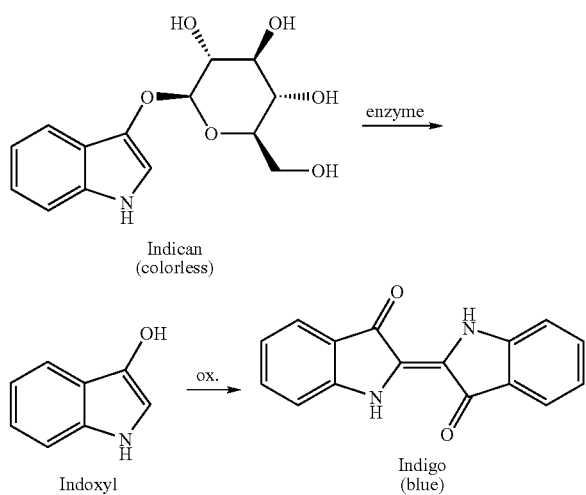

Also, the principles known from vat dyes for coloring textiles can be used in an enzyme-based TTI according to the instant invention. Vat dyes are dyes which are applied to the textile substrate in reduced, soluble form and then oxidize to the original insoluble pigment. Common vat dyes are quinonic dyes and particularly common are anthraquinones and indigoids. These dyes are essentially insoluble in water and incapable of dyeing fibres directly. However, reduction in alkaline liquor produces the water soluble alkali metal salt of the dye. In this leuco form these dyes have an affinity for the textile fibre. Subsequent oxidation reforms the original insoluble dye. They are called vat dyes because, being originally insoluble in water, they undergo special preparation in large vats before the cloth is introduced; here they are made soluble, usually by the adding of caustic soda and hyposulphite. In this mixture or dye liquor the textiles are soaked. Certain chemicals are thereafter added, changing the dyestuff back to the insoluble form in the cloth or fiber. This is called the fixing process. All the vat dyes are fast, especially to washing.

For example, the hydrolysis of the bond between O and R''' in

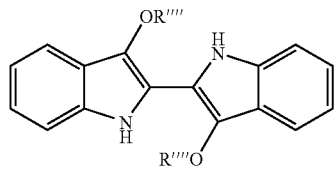

which may be an ether bond, an ester bond or the oxygen may be linked to the glycosidic carbon atom of a sugar moiety can be hydrolyzed by the catalytic activity of an ether hydrolyse, an carboxylic esterase and a glycosylase, respectively. The so formed enol form will undergo tautomerization to the keto form and will subsequently be oxidized by oxygen present in the air (see below). It will be understood that the cleavable bond between O and R''' is of course not limited to the aforementioned bonds but also includes other types of ester bonds like thioesters esters of the phosphorous and other acids as well as acid anhydrides.

Vat Dyes Principle:

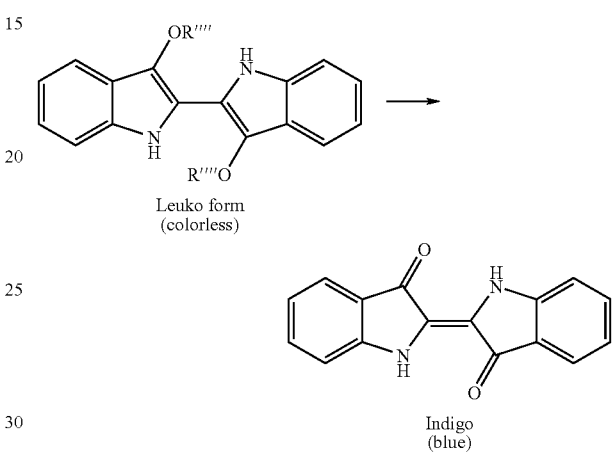

It will further be understood that the above described principle and its use in an enzyme-based TTI according to instant invention is not limited to indigo but for example also includes the chemistry of C.I.Pigment Blue 60 (indanthrone):

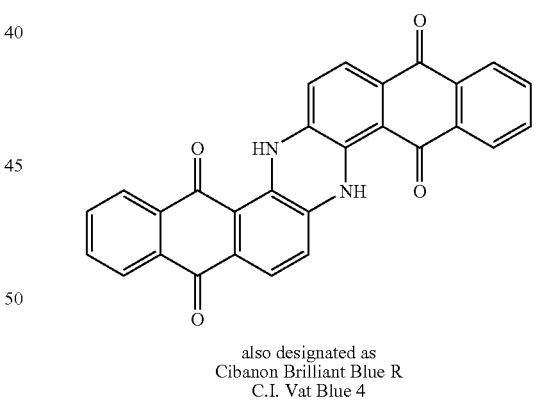

also designated as
Cibanon Brilliant Blue R
C.I. Vat Blue 4

The pigment form of C.I. Pigment Blue 60 is also obtained from the corresponding leuco form.

Additional preferred enzymes for the enzyme-based TTI according to the instant invention include alkaline phosphatase (AP), peroxidase (POD) and β-galactosidase (β-Gal). Suitable substrates for these enzymes are 4-nitrophenyl phosphate (pNPP), 4-methylumbelliferyl phosphate (MUP) and 5-bromo-4-chloro-3-indolyl phosphate (BCIP) for alkaline phosphatase; 3,3',5,5'-tetramethylbenzidine (TMB) and 2,2'-azino-di-[3-ethylbenzthiazoline-6-sulfonate] (ABTS) for peroxidase; and chlorophenol-red-beta-D-galactopyranoside (CPRG) for β-galactosidase.

Both the aforementioned marker enzymes and the corresponding substrates can be purchased from Roche Diagnostics GmbH Penzberg, Germany. For example, POD is available as lyophilized peroxidase from horse-radish as well as a lyophilized preparation of polymerized (approx. 20 POD molecules) and MH-activated POD for better sensitivity. MH-activated Poly POD can be used directly for conjugation with sulfhydryl groups. Further, β-galactosidase can be purchased as lyophilized recombinant β-galactosidase expressed in *Escherichia coli*. Although, native AP isolated from bovine intestine can be used, it is preferred to utilize recombinant AP derived from the expression of bovine intestine alkaline phosphatase as a highly active enzyme in the yeast *Pichia pastoris*. Alkaline phosphatase is a homodimeric orthophosphoric-monoester phosphohydrolase that catalyzes the hydrolysis of numerous phosphate esters, such as esters of primary and secondary alcohols, saccharides, cyclic alcohols, phenols and amines. Phosphodiesters do not react. The enzyme also hydrolyzes inorganic pyrophosphate. The kinetic properties of the enzyme depend on many factors, such as purity of enzyme, concentration of enzyme, buffer, pH etc.

Both 3,3',5,5'-tetramethyl benzidine (TMB) and 2,2'-azino-di-[3-ethylbenzthiazoline-6-sulfonate] are suitable POD substrates. TMB forms a soluble pale blue reaction product which is detectable at 370 nm. By stopping the POD reaction with sulfuric acid, the reaction product can be measured at 450 nm. ABTS forms a soluble green reaction product which is detectable at 405 nm. TMB and ABTS can be purchased from Roche as crystalline powders. Chlorophenol-red-β-D-galactopyranoside (CPRG) is a suitable chromogenic β-Gal substrate that forms a soluble reaction product detectable at 405 nm. 4-Nitrophenyl phosphate (pNPP) is a chromogenic AP substrate that forms a soluble yellow-colored reaction product detectable at 405 nm. The pNPP reaction can be stopped with NaOH before detection. Further, 4-methylumbelliferyl phosphate (MUP) is a fluorogenic AP substrate It forms the soluble fluorescent reaction product methylumbelliferone, which can be measured by fluorometric detection with excitation at 360 nm and emission at 450 nm. Also, 5-bromo-4-chloro-3-indolyl phosphate (BCIP) is a suitable AP substrate that forms an insoluble dark blue reaction product. 5-Bromo-4-chloro-3-indolyl phosphate is dephosphorylated by the alkaline phosphatase to 5-bromo-4-chloro-3-indoxyl. The reaction product reacts further spontaneously with oxygen to form an insoluble dark blue indigo-dye. The blue precipitate is insoluble in aqueous systems. Instead od oxygen, other electron acceptors may be used, e.g. nitro blue tetrazolium chloride (NBT). Since NBT is also converted by the reduction process to a blue insoluble precipitate, enhanced color development and increased detection sensitivity are observed when BCIP and NBT are combined.

In a preferred embodiment of the present invention, the enzyme of the time temperature indicator is directly incorporated into a packaging material or a label and the substrate is provided in an ink formulation which is directly printed onto said packaging material or label. More preferably, the enzyme is immobilized on or within the packaging material or label by covalent bonds, complex formation and/or adhesion.

Preferably, the packaging material or the label comprise a carrier matrix which in principle can be any substance capable of being immobilized with the enzyme. Thus, the matrix can take on many known forms, such as those utilized for reagent strips for solution analysis. For example, U.S. Pat. No. 3,846,247 teaches the use of felt, porous ceramic strips and woven or matted glass fibers. As substitutes for paper, U.S. Pat. No. 3,522,928 teaches the use of wood sticks, cloth, sponge material and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. The French Pat. No. 2,170,397 teaches the use of carrier matrices having greater than 50% polyamide fibers therein. Another approach to carrier matrices is disclosed in U.S. Pat. No. 4,046,513, wherein the concept of printing reagents onto a suitable carrier matrix is employed. U.S. Pat. No. 4,046,514 discloses the interweaving or knitting of filaments bearing reagents in a reactant system. It is, therefore, to be appreciated that in producing a time temperature indicator of the invention all such carrier matrix concepts can be employed, as can others.

Enzymes are generally expensive and relatively unstable compared to most chemical compounds, even when they are used in aqueous media where enzymes normally function. In addition, enzymes are difficult to store in a manner that retains their activity and functional integrity, for commercially reasonable periods of time (months to years) without having to resort to refrigeration (−80° C. to liquid N2 temperatures), or to maintenance in aqueous solvents of suitable ionic strength, pH, etc.

To circumvent these disadvantages, enzyme immobilization techniques can be used to attach the enzyme on or within a solid support material, for example the packaging material or the label. Immobilization can improve the stability of enzyme catalysts and protect their functional integrity even in harsh solvent environments and under extreme temperatures characteristic for some applications (Hartmeier, W., Trends in Biotechnology 3: 149-153 (1985)).

A number of useful reviews of enzyme immobilization methods have appeared in the literature (Maugh, T. H., Science 223: 474-476 (1984); Tramper, J., Trends in Biotechnology 3: 45-50 (1985)). Maugh describes five general approaches to the immobilization of enzymes. These include: adsorption on solid supports (such as ion-exchange resins); covalent attachments to supports (such as ion-exchange resins, porous ceramics or glass beads); entrapment in polymeric gels; encapsulation; and the precipitation of soluble proteins by cross-linking them with bifunctional reagents in a random and undefined manner. In addition, one can immobilize whole cells (usually dead and made permeable) which have expressed the desired enzyme activity at high levels (e.g., Nagasawa, T. and Yamada, H., Trends in Biotechnology 7: 153-158 (1989)).

In principle, each of these immobilization procedures can be used for immobilizing the enzyme of the time temperature indicator according to the present invention.

One approach to immobilize the enzyme is to covalently bind the polypeptide on the surface of a carrier material. See for example, H. H. Weetal, "Preparation of Immobilized Proteins Covalently Coupled Through Silane Coupling Agents to Inorganic Supports," Applied Biochem. and Biotech. 41:157 (1993). Also, a material can be used that comprises a porous support wherein the enzyme is immobilized upon or within by covalent bonds to the porous support. For example, a foamed polyurethane product that contains the enzyme internally bound thereto is suitable. This material can be prepared by a method which includes contacting, prior to the subsequent foaming step, an isocyanate-capped polyurethane with an aqueous dispersion of the enzyme, under foam-forming conditions, whereby the polyurethane foams and the enzyme becomes integrally bound to the thus formed polyurethane foam. The isocyanate-capped polyurethane can be the reaction product of toluene diisocyanate and a polyhydroxy compound selected from the group consisting of polyoxybutylene polyol polymer, ethylene glycoldiethylene glycol, polyoxyethylene polyol polymer, pentaerythritol, glycerol, trimethylol propane and polyoxypropylene polyol polymer.

On being intimately contacted with the aqueous enzyme dispersion, the isocyanate-capped polyurethane becomes chemically very active. Some of its free isocyanate groups react with the amine groups of the enzyme, and some react with water to give carbon dioxide and to form amine groups on the polyurethane molecule. These latter amine groups react with free isocyanate groups on neighboring polyurethane molecules, and this reaction (forming a urea linkage) will cause further growth of the polyurethane and will also introduce cross links between the polyurethane molecules. Other additives such as crosslinking agents (polyamines, polythiols, polyacids) or antioxidants, fillers, etc. may also be present during foaming.

Alternatively, the enzyme of the time temperature indicator can be immobilized on or within a solid support material, for example a packaging material or a label via avidin-biotin-complexes formed by the biotin moiety of the biotinylated enzyme and avidin polypeptides attached to the surface of a packaging material or label.

The surface of a packaging material or a label coated with avidin can be used as a carrier for enzymatic reactions within the time temperature indicator format. Because the biotin-streptavidin interaction is both specific and strong (Kd=10<−15>M), biotinylated enzymes adhere specifically to the space of deposition. Biotin is easily incorporated into polypeptides to obtain biotinylated enzymes by using a biotin-protein ligase enzyme that activates biotin to form biotinyl 5' adenylate and transfers the biotin to biotin-accepting proteins.

Avidin and biotin derivatives which can be used to prepare the modified packaging material or label include streptavidin, succinylated avidin, monomeric avidin, biocytin (that is, biotin-epsilon-N-lysine), biocytin hydrazide, amine or sulfhydryl derivatives of 2-iminobiotin and biotinyl-epsilon-aminocaproic acid hydrazide. Biotin derivatives, such as biotin-N-hydroxysuccinimide ester, biotinyl-epsilon-aminocaproic acid-N-hydroxysuccinimide ester, sulfosuccinimidyl 6-(biotin amido)hexanoate, N-hydroxysuccinimideiminobiotin, biotinbromoacetylhydrazide, p-diazobenzoyl biocytin and 3-(N-maleimidopropionyl)biocytin, can also be attached to couple enzymes on the modified surface.

In a specific embodiment of the invention, the enzyme of the time temperature indicator is a stable, freeze-dried formulation of the immobilized enzyme that comprises a buffer and at least one cryoprotectant, preferably alanine and mannitol, in which the mass ratio of mannitol to alanine ranges from 0.1 to 1.

Freeze drying, or lyophilization, is a dehydration technique. It takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Freeze drying has become an accepted method of processing heat sensitive products, e.g. enzymes, that require long term storage at temperatures above freezing. Steps in freeze drying include pretreatment, freezing, primary drying and secondary drying.

Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide cryoprotection for reactive products. The term "cryoprotection" refers to stabilization during all of the freeze drying process (i.e., during both freezing and drying).

The second step is to freeze the product. Freezing the product decreases chemical activity by decreasing molecular movement. Freezing is essentially the dehydration step in freeze drying; once the solvent matrix is in the solid (frozen) state, the solute matrix is "dry," (although it may contain some bound water. A rule of thumb for freezing product is that the product container should preferably not be filled with product to more than half of its total volumetric rating. In practice this may also mean filling the product only to certain depth to facilitate freezing, ice sublimation and final water/solvent removal. This helps insure, in most cases, that the surface to depth ratio is such that freeze drying is not impeded by the product depth.

The primary drying may begin with the sublimation of ice crystals at low pressure and at temperatures low enough to reduce cake softening and collapse. After removal of the ice crystals by sublimation, the remaining matrix may still contain bound water/solvent that may be removed by slow heating under low pressure conditions. The drying temperature may be gradually increased as the water content in the dried matrix decreases. Any local overheating of the product matrix may cause localized product deterioration and/or collapse. When the product reaches a temperature above 0° C., secondary drying may have already begun. A product in secondary drying often appears dry. However, some "bound" solvent may still remain in the apparently dry product. During secondary drying, a vacuum pump creates a low pressure condition that promotes removal of bound solvents. The amount of residual water or solvent in the lyophilized product is dependent on the length of time the product remains in secondary drying. Final level of water/solvent content is important for product storage, e.g. if the water content is too high the product matrix may experience melting and collapse if the storage temperature is increased. Uniformity of water/solvent removal across large areas and volumes of product is thus very important to protect product from local deterioration during lyophilized product storage at ambient temperatures.

It is known that the formulation has a considerable effect on the degradation of proteins during freeze-drying, as well as a high impact on their stability in freeze-dried form. Various formulation variables which affect these parameters are mainly the pH, the quantity of salts present, the type and the quantity of excipients, the type of cryoprotection chosen, as well as the temperatures, pressure and time which are chosen for the freezing, sublimation and desiccation operations. These different variables influence the physical state of the freeze-dried product obtained, namely: vitreous amorphous, soft amorphous, crystalline or a combination of these states.

Alanine, in crystallized form, has the advantage of preventing the collapse of the freeze-dried product during sublimation and desiccation and allows the production of a freeze-dried product with a larger specific surface area and therefore allows a more rapid desiccation (Pikal M. J., Freeze-drying of proteins, Biopharm. 26-30 Oct. 1990). The presence of mannitol in amorphous form surrounding the protein guarantees the presence of noncrystallized water linked to the protein, during freezing, and thereby prevents the denaturation of the protein. Furthermore, the presence of polyols stabilizes the proteins against thermal degradations, through hydrophobic interactions (Back J. F., Oakenfull D., Smith M. B., Increased thermal stability of proteins in the presence of sugars and polyols, Biochemistry, 1979, 18, 23, 5191-96).

The combined use of alanine and mannitol allow to obtain a stable freeze-dried product containing the enzyme which is cryoprotected by an amorphous solid phase during freezing, consisting essentially of protein and mannitol, this amorphous phase coexisting in the freeze-dried product obtained after sublimation and desiccation of the frozen solution, with a crystalline phase consisting essentially of alanine.

The time temperature indicator according to the present invention is preferably packaged and/or attached to perishable items, especially to pharmaceuticals, biologicals or food stuffs.

The enzyme of the time temperature indicator is preferably provided in association with the substrate in a range of concentrations, such that the rate of colour change varies only with time given a constant temperature. Especially, the time temperature indicator is embodied in a format in which colour change progresses along or around the format in accordance with prevailing time temperature conditions.

In another embodiment, the present invention also relates to a method of time temperature indication comprising the step of an enzyme-catalyzed reaction of a substrate of said enzyme to a reaction product in a time and temperature dependent manner, wherein the formation of the reaction product is detected by monitoring a physical characteristic of the substrate and/or the product which corresponds to its concentration and wherein the enzyme is immobilized on or within a solid support.

Preferably, the formation of the reaction product is visualized by a change of color based on the color difference between the substrate and the product.

In a preferred form of the method of time temperature indication, the enzyme is directly incorporated into a packaging material or a label and the substrate is provided in an ink formulation which is directly printed onto the packaging material or label. More preferably, the enzyme is immobilized on or within a packaging material or label by covalent bonds, complex formation and/or adhesion.

The present invention also relates to a printing ink or printing ink concentrate that comprises at least one substrate of an enzyme of a time-temperature indicator, wherein the reaction of the substrate catalyzed by the immobilized enzyme in a time and temperature dependent manner produces a reaction product which can be detected by monitoring a physical characteristic of the substrate and/or the product which corresponds to its concentration. Preferably, the printing ink or printing ink concentrate according to the present invention also comprises a buffer system and/or enzyme-specific cofactors.

The printing inks according to the invention comprise the substrate, especially the substrates of alkaline phosphatase, peroxidase and β-galactosidase compounds in a concentration of from 0.01 to 100 µM, preferably from 0.05 to 50 µM, especially from 0.1 to 10 µM, more especially from 1 to 5 µM, and can be used, for example, for electrophotography, intaglio printing, flexographic printing, screen printing, offset printing or letterpress printing.

The printing ink is, for example, a liquid or paste-form dispersion comprising colorant (indicator), binder and optionally solvent and/or optionally water and additives. In a liquid printing ink, the binder and, where applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

The printing inks can be used, for example, for electrophotography, intaglio printing, flexographic printing, screen printing, offset printing, lithography or letterpress printing. Suitable printing inks are both solvent-based printing inks and water-based printing inks. Of interest are, for example, printing inks based on aqueous acrylates. Such inks are to be understood as including polymers or copolymers that are obtained by polymerisation of at least one monomer containing a group

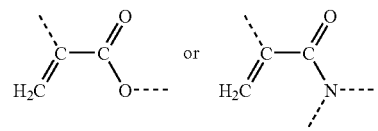

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclohexanone, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations. For intaglio or flexographic printing, a printing ink is usually prepared by dilution of a printing ink concentrate and can then be used in accordance with methods known per se. The printing inks may, for example, also comprise alkyd systems that dry oxidatively. The printing inks are dried in a known manner customary in the art, optionally with heating of the coating. A suitable aqueous printing ink composition comprises, for example, an enzyme-specific substrate, a dispersant and a binder.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids.

The arylsulfonic acid/formaldehyde condensation products are obtainable, for example, by sulfonation of aromatic compounds, such as naphthalene itself or naphthalene-containing mixtures, and subsequent condensation of the resulting arylsulfonic acids with formaldehyde. Such dispersants are known and are described, for example, in U.S. Pat. No. 5,186,846 und DE-A-197 27 767. Suitable oxalkylated phenols are likewise known and are described, for example, in U.S. Pat. No. 4,218,218 und DE-A-197 27 767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol. It is also possible, for example, to use polymeric acids which act both as dispersants and as binders.

Examples of suitable binder components that may be mentioned include acrylate-group-containing, vinyl-group-containing and/or epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity, the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary in the printing and coating industries, for example preservatives (such as glutaric dialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≦1% by weight, based on the weight of the preparation.

The printing inks may also, for example, comprise solubilisers, e.g. ε-caprolactam. The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 5 to 9, especially from 6.5 to 8.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

Printing materials that may be mentioned include, for example:
- cellulosic materials, such as paper, paperboard, cardboard, which may also be varnished or have some other coating,
- metallic materials, such as foils, sheets or workpieces of aluminium, iron, copper, silver, gold, zinc or alloys of those metals, which may be varnished or have some other coating,
- silicate materials, such as glass, china and ceramics, which may likewise be coated,
- polymeric materials of all kinds, such as polystyrene, polyamides, polyester, polyethylene, polypropylene, melamine resins, polyacrylates, polyacrylonitrile, polyurethanes, polycarbonates, polyvinyl chloride and corresponding copolymers and block copolymers,
- textile materials, knitted goods, woven goods, non-wovens and made-up goods of polyester, modified polyester, polyester blends, cellulosic materials, such as cotton, cotton blends, jute, flax, hemp and ramie, viscose, wool, silk, polyamide, polyamide blends, polyacrylonitrile, triacetate, acetate, polycarbonate, polypropylene, polyvinyl chloride, polyester microfibres and glass fibre fabrics,
- foodstuffs and cosmetics.

Especially suitable printing materials are e.g. paper, coated paper, cardboard and plastic or metal foils, such as aluminium foils.

Preference is given to printing processes wherein aqueous printing inks are used. The printing of the printing material is preferably effected by means of continuos or dropwise ink-jet printing. Aqueous ink-jet inks are preferred.

The inks may be non-aqueous inks which consist of a solution of the enzyme of the time temperature indicator in an organic solvent or a mixture of organic solvents. Examples of solvents that can be used for this purpose are alkyl carbitols, alkyl cellosolves, dialkylformamides, dialkylacetamides, alcohols, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, butyl acetate, triethyl phosphate, ethyl glycol acetate, toluene, xylene, Tetralin or petroleum ether fractions. Examples of solid waxes as solvents that, as ink vehicles, have to be heated first, are stearic or palmitic acid.

The inks may comprise water-miscible organic solvents, for example $C_1$-$C_4$alcohols, e.g. methanol, ethanol, n-propanol, isopropanol, n-butanol, sec-butanol, tert-butanol or isobutanol; amides, e.g. dimethylformamide or dimethylacetamide; ketones or ketone alcohols, e.g. acetone, diacetone alcohol; ethers, e.g. tetrahydrofuran or dioxane; nitrogen-containing heterocyclic compounds, e.g. N-methyl-2-pyrrolidone or 1,3-dimethyl-2-imidazolidone, polyalkylene glycols, e.g. polyethylene glycol, or polypropylene glycol; $C_2$-$C_6$alkylene glycols and thioglycols, e.g. ethylene glycol, propylene glycol, butylene glycol, triethylene glycol, thiodiglycol, hexylene glycol and diethylene glycol; further polyols, e.g. glycerol or 1,2,6-hexanetriol; and $C_1$-$C_4$alkyl ethers of polyvalent alcohols, e.g. 2-methoxyethanol, 2-(2-methoxyethoxy)ethanol, 2-(2-ethoxyethoxy)ethanol, 2-[2-(2-methoxyethoxy)ethoxy]-ethanol or 2-[2-(2-ethoxyethoxy)ethoxy]ethanol; preferably N-methyl-2-pyrrolidone, diethylene glycol, glycerol or especially 1,2-propylene glycol, usually in an amount of from 2 to 30% by weight, especially from 5 to 30% by weight and preferably from 10 to 25% by weight, based on the total weight of the ink.

The inks may also comprise solubilisers, e.g. ε-caprolactam. The printing inks may, inter alia for the purpose of adjusting the viscosity, comprise thickeners of natural or synthetic origin.

Furthermore, the pigment preparations according to the invention, especially when binder curing is to be effected by means of UV radiation, may comprise a photoinitiator which initiates the polymerisation.

Suitable photoinitiators for free radical photopolymerisations, that is to say the polymerisation of acrylates and, if desired, vinyl compounds, are e.g. benzophenone and benzophenone derivatives, such as 4-phenylbenzophenone and 4-chlorobenzophenone, acetophenone derivatives, such as 1-benzoylcyclohexan-1-ol, 2-hydroxy-2,2-dimethylacetophenone and 2,2-dimethoxy-2-phenylacetophenone, benzoin and benzoin ethers, such as methyl, ethyl and butyl benzoin ethers, benzil ketals, such as benzil dimethyl ketal, 2-methyl-1-[4-(methylthio)phenyl]-2-morpholinopropan-1-one, acylphosphine oxides, such as 2,4,6-trimethylbenzoyl-diphenylphosphine oxide and bisacylphosphine oxides.

Suitable photoinitiators for cationic photopolymerisations, that is to say the polymerisation of vinyl compounds or epoxy-group-containing compounds, are, for example, aryidiazonium salts, such as 4-methoxybenzenediazonium hexafluorophosphate, benzenediazonium tetrafluoroborate and toluenediazonium tetrafluoroarsenate, aryliodonium salts, such as diphenyliodonium hexafluoroarsenate, arylsulfonium salts, such as triphenylsulfonium hexafluorophosphate, benzene- and toluene-sulfonium hexafluorophosphate and bis[4-diphenylsulfonio-phenyl]sulfide-bis-hexafluorophosphate, disulfones, such as diphenyl disulfone and phenyl-4-tolyl disulfone, diazodisulfones, imidotriflates, benzoin tosylates, isoquinolinium salts, such as N-ethoxyisoquinolinium hexafluorophosphate, phenylpyridinium salts, such as N-ethoxy-4-phenylpyridinium hexafluorophosphate, picolinium salts, such as N-ethoxy-2-picolinium hexafluorophosphate, ferrocenium salts, and titanocenes.

When a photoinitiator is present in the ink compositions according to the invention, which is generally necessary for binder curing by UV radiation, the content thereof is generally from 0.1 to 10% by weight, preferably from 0.1 to 8% by weight.

Examples of thickeners that may be mentioned include commercially available alginate thickeners, starch ethers or locust bean flour ethers, especially sodium alginate on its own or in admixture with modified cellulose, for example methyl-, ethyl-, carboxymethyl-, hydroxyethyl-, methylhydroxyethyl-, hydroxypropyl- or hydroxypropylmethyl-cellulose, especially having preferably from 20 to 25% by weight carboxymethylcellulose. Synthetic thickeners that may be mentioned are, for example, those based on poly(meth)acrylic acids or poly(meth)acrylamides.

The inks comprise such thickeners e.g. in an amount of from 0.01 to 2% by weight, especially from 0.01 to 1% by weight and preferably from 0.01 to 0.5% by weight, based on the total weight of the ink.

It is also possible for the inks to comprise buffer substances, for example borax, borate, phosphate, polyphosphate or citrate. Examples include borax, sodium borate, sodium tetraborate, sodium dihydrogen phosphate, disodium hydrogen phosphate, sodium tripolyphosphate, sodium pentapolyphosphate and sodium citrate. They are used especially in amounts of from 0.1 to 3% by weight, preferably from 0.1 to 1% by weight, based on the total weight of the ink, in order to establish a pH value of e.g. from 4 to 9, especially from 5 to 8.5.

As further additives, the inks may comprise surfactants or humectants.

As surfactants there come into consideration the commercially available anionic or non-ionic surfactants. Suitable humectants in the inks according to the invention include, for example, urea or a mixture of sodium lactate (advantageously in the form of a 50 to 60% aqueous solution) and glycerol and/or propylene glycol in amounts of preferably from 0.1 to 30% by weight, especially from 2 to 30% by weight.

Furthermore, the inks may also comprise customary additives, for example preservatives (such as glutaric dialdehyde and/or tetramethylolacetyleneurea), anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. Such agents are usually used in amounts of from 0.01 to 1% by weight, based on the total weight of the ink.

The inks can be prepared in customary manner by mixing together the individual constituents in the desired amount of water.

The inks according to the invention are especially suitable for use in recording systems of the kind in which an ink is expressed from a small opening in the form of droplets which are directed towards a substrate on which an image is formed. Suitable substrates are, for example, paper, textile fibre materials, metal foils or plastics foils. Suitable recording systems are e.g. commercially available ink-jet printers for use in paper or textile printing.

Depending upon the nature of the use, it may be necessary for e.g. the viscosity or other physical properties of the ink, especially those properties which influence the affinity of the ink for the substrate in question, to be adapted accordingly.

In ink-jet printing, individual droplets of ink are sprayed onto a substrate in a controlled manner from a nozzle. For this purpose, predominantly the continuous ink-jet method and the drop-on-demand method are used. In the continuous ink-jet method, the droplets are produced continuously and any droplets not required for the printing are conveyed to a collecting vessel and recycled. In the drop-on-demand method, however, droplets are produced and printed as required; that is to say droplets are produced only when required for the printing. The production of the droplets can be effected, for example, by means of a piezo-inkjet head or by means of thermal energy (bubble jet).

The subsequent curing of the binder, that is to say the fixing of the print, can be effected in customary manner with the aid of heat or high-energy radiation. For this purpose, the print is irradiated either with electrons under an inert gas atmosphere (e.g. nitrogen) (electron beam curing) or with high-energy electromagnetic radiation, preferably in a wavelength range of from 220 to 450 nm. In such a procedure, the chosen light intensities should be matched to the curing speed in order to avoid decomposition of the indicator.

Another embodiment of the present invention concerns a packaging material or a label that comprises an enzyme which is directly incorporated into the packaging material or the label. Preferably, the enzyme is immobilized on or within the packaging material or label by covalent bonds, complex formation and/or adhesion.

In yet another embodiment, the present invention also relates to a method of printing a packaging material or a label, comprising the steps of:

(a) optionally printing onto the packaging material or label a solution which comprises an enzyme, (b) optionally immobilizing the enzyme on or within the packaging material or label by forming covalent bonds, complex formation and/or adhesion of the enzyme to the packaging material or label, and (c) printing onto the packaging material or label comprising the immobilized enzyme a solution which comprises a substrate of the enzyme, wherein the reaction of the substrate catalyzed by the enzyme produces a reaction product in a time and temperature dependent manner and wherein the formation of the reaction product can be detected by monitoring a physical characteristic of the substrate and/or the product which is linked to its concentration.

When ink-jet printing is used, the procedure is advantageously as follows:

In Step a), a solution which comprises at least one enzyme which is capable to convert an enzyme-specific substrate so as to directly produce a reaction product having a different color than the substrate, as defined above, is applied by means of ink-jet printing to the packaging material or label, especially to the packaging or to labels that are applied to such packaging material of ageing- and temperature-sensitive products.

In a preferred embodiment, in Step a) it is possible additionally to apply, by means of ink-jet printing, a reference scale which reproduces the change in the colour of the indicator as a function of time, and it is possible to apply, preferably in black ink, further text (or information), such as an expiry date, product identification, weight, contents etc.

Step a) is followed by Step b) wherein the enzyme is immobilized on or within the packaging material or label by forming covalent bonds, complex formation and/or adhesion of the enzyme to the packaging material or label. Preferably, the enzyme of the time temperature indicator is immobilized via avidin-biotin-complexes formed by the biotin moiety of the biotinylated form of the enzyme of step a) and avidin polypeptides attached to the surface of a packaging material or label. Because the biotin-streptavidin interaction is both specific and strong (Kd=10<−15>M), the biotinylated enzyme is firmly bound to the solid avidin-modified support.

Step b) is followed by the application of an enzyme-specific substrate wherein the reaction of the substrate catalyzed by the immobilized enzyme produces a reaction product in a time and temperature dependent manner and wherein the formation of the reaction product can be detected by monitoring a physical characteristic of the substrate and/or the product which is linked to its concentration. Preferably, 4-Nitrophenyl phosphate (pNPP) is used as a chromogenic substrate when the enzyme of step a) is alkaline phosphatase. The conversion of pNPP by AP results in a yellow-colored reaction product that is easily detectable at 405 nm.

By means of the reference scale printed with the time-temperature indicator, absolute determination of quality grades is possible. The time-temperature indicator and the reference scale are advantageously arranged on a light-coloured packaging material or label in order to facilitate reading.

For example, in Step a) and in Step c) a printing ink, a printing ink concentrate and/or an ink-jet ink comprising the enzyme and the substrate as described above can be applied to the packaging of ageing- and temperature-sensitive products in the form of a barcode. The time- and/or temperature-induced decoloration or coloration of the indicator is advantageously so adjusted that once the expiry date has been passed, the barcode can no longer be read by a scanner. Alternatively, the time- and/or temperature-dependent decoloration of the indicator can also bring about a change in the barcode such that it can still be read, but, on being read, the information relating to the expiry date is given.

The present invention also concerns a method of determining the quality of an ageing- and temperature-sensitive product, comprising the steps of:
(a) printing onto a packaging material or an label comprising an enzyme which is directly incorporated into the packaging material or the label a printing ink or printing ink concentrate comprising at least one substrate for the immobilized enzyme, wherein the reaction of the substrate catalyzed by the enzyme in a time and temperature dependent manner produces a reaction product and wherein the formation of the reaction product is detected by monitoring a physical characteristic of the substrate and/or the product which corresponds to its concentration, and
b) determining the degree of time- or temperature-induced reaction product formation and deducing the quality of the ageing- and temperature-sensitive product from the degree of reaction product formation.

It is preferred when the quality of the product is determined by evaluating the degree of decoloration or coloration with the aid of a reference scale.

The coloration of the indicator can take place at a defined timepoint, preferably, for example, immediately after printing the substrate in Step c), which is especially the packaging of a perishable material.

The time-temperature clock can accordingly be started at a defined desired timepoint. Decoloration is preferred for consideration according to the invention, but the use of an indicator in which the coloration process forms the basis of the time-temperature dock is also conceivable.

The actual determination of the quality of ageing- or temperature-sensitive products is preceded by the activation of the indicator in Step c). At a later timepoint, the degree of time- or temperature-induced decoloration is then measured and the quality of the product is inferred therefrom. When an evaluation is made with the aid of the human eye, it may be advantageous to arrange e.g. alongside or below the substrate a reference scale which allocates a certain quality grade, a certain timepoint etc. to a certain degree of decoloration.

The method according to the invention is suitable for marking perishable products such as foodstuffs (e.g. frozen foods), medicaments, drugs, transplant organs and perishable raw materials.

The invention claimed is:
1. A time temperature indicator for indicating temperature change over time, comprising an immobilized enzyme, wherein the enzyme is an amidase, a lipase, a glycosylase, a carboxylic esterase or an ether hydrolase, and a substrate of the enzyme, said substrate being a pigment precursor selected from the group consisting of
(a) a compound of general formula (I)

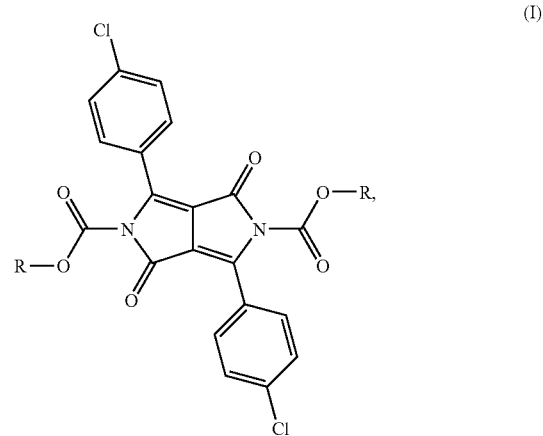

wherein R is an unsubstituted or substituted, aliphatic or aromatic residue and (b) a compound of general formula (II)

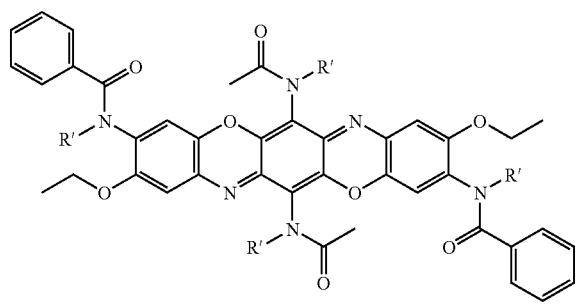

wherein

wherein R" is an unsubstituted or substituted, aliphatic or aromatic residue or

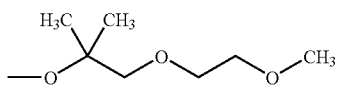

wherein the reaction of the substrate catalyzed by the enzyme produces a reaction product in a time and temperature dependent manner and wherein the formation of the reaction product can be detected by monitoring a physical characteristic of the substrate and/or the product which is linked to its concentration.

2. The time temperature indicator of claim 1, wherein the enzyme-catalyzed reaction produces a reaction product that is a different color than the substrate.

3. The time temperature indicator of claim 1, wherein the enzyme is directly incorporated into a packaging material or a label and the substrate is provided in an ink formulation which is directly printed onto said packaging material or label.

4. The time temperature indicator of claim 3, wherein the enzyme is immobilized on or within the packaging material or label by covalent bonds, complex formation and/or adhesion.

5. The time temperature indicator of claim 1 wherein the enzyme is a carboxylic esterase or an ether hydrolase.

\* \* \* \* \*

UNITED STATES PATENT AND TRADEMARK OFFICE
CERTIFICATE OF CORRECTION

PATENT NO.         : 7,736,866 B2                                    Page 1 of 1
APPLICATION NO.    : 11/659645
DATED              : June 15, 2010
INVENTOR(S)        : Hans Reichert et al.

It is certified that error appears in the above-identified patent and that said Letters Patent is hereby corrected as shown below:

Column 21, line 20 reads "  " should read --  --

Signed and Sealed this
Twenty-fifth Day of January, 2011

David J. Kappos
*Director of the United States Patent and Trademark Office*